United States Patent
Lidgren et al.

(10) Patent No.: US 8,662,737 B2
(45) Date of Patent: Mar. 4, 2014

(54) DEVICE FOR PRODUCING A HARDENABLE MASS

(75) Inventors: Lars Lidgren, Lund (SE); Sven Jönsson, Staffanstorp (SE); Torony Lundgren, Eslöv (SE); Fritz Brorsson, Flyinge (SE); Östen Gullwi, Löddeköpinge (SE)

(73) Assignee: Bone Support AB, Lund (SE)

( * ) Notice: Subject to any disclaimer, the term of this patent is extended or adjusted under 35 U.S.C. 154(b) by 0 days.

(21) Appl. No.: 13/613,563

(22) Filed: Sep. 13, 2012

(65) Prior Publication Data

US 2013/0064033 A1 Mar. 14, 2013

Related U.S. Application Data

(62) Division of application No. 12/585,194, filed on Sep. 8, 2009, now Pat. No. 8,297,831, which is a division of application No. 11/587,313, filed as application No. PCT/SE2005/000932 on Jun. 17, 2005, now Pat. No. 7,938,572.

(30) Foreign Application Priority Data

Jun. 22, 2004 (SE) .................................... 0401604-4

(51) Int. Cl.
*B01F 15/02* (2006.01)
(52) U.S. Cl.
USPC .......................................................... 366/189
(58) Field of Classification Search
USPC .......... 366/189, 139; 222/386, 390, 391, 137, 222/236
See application file for complete search history.

(56) References Cited

U.S. PATENT DOCUMENTS

| 949,163 A | 2/1910 | Stapley |
| 1,644,173 A | 10/1927 | Carr |
| 1,865,912 A | 7/1932 | Horn |

(Continued)

FOREIGN PATENT DOCUMENTS

| DE | 44 09 610 | 9/1995 |
| DE | 202 16 632 | 3/2004 |

(Continued)

OTHER PUBLICATIONS

Notice of Allowance in U.S. Appl. No. 12/585,194 dated Jun. 22, 2012; (7 pages).

(Continued)

*Primary Examiner* — Tony G Soohoo
(74) *Attorney, Agent, or Firm* — Finnegan, Henderson, Farabow, Garrett & Dunner L.L.P.

(57) ABSTRACT

The present invention relates to a device for producing a hardenable mass, preferably bone substitute and/or bone reinforcing material or bone cement or similar material. A mixing container may include a mixing space in which at least one powder and at least one liquid component are mixed to provide the hardenable mass. A piston may be provided in the mixing space of the mixing container. A screw device may be connectable to the mixing container such that the screw device may be configured to impart by screw movements a discharge movement to the piston to discharge the hardenable mass from the mixing space.

10 Claims, 9 Drawing Sheets

(56) References Cited

U.S. PATENT DOCUMENTS

| | | | |
|---|---|---|---|
| 2,545,017 | A | 3/1951 | Billingsley |
| 3,367,783 | A | 2/1968 | Billerbeck |
| 3,475,010 | A | 10/1969 | Cook et al. |
| 3,570,719 | A * | 3/1971 | Schiff ............... 222/390 |
| 3,688,765 | A | 9/1972 | Gasaway |
| 3,837,379 | A | 9/1974 | McDonald et al. |
| 3,965,910 | A | 6/1976 | Fischer |
| 4,001,323 | A | 1/1977 | Felder et al. |
| 4,139,605 | A | 2/1979 | Felder et al. |
| 4,240,425 | A | 12/1980 | Akhavi |
| 4,269,331 | A | 5/1981 | Watson |
| 4,338,925 | A | 7/1982 | Miller |
| 4,348,377 | A | 9/1982 | Felder et al. |
| 4,487,766 | A | 12/1984 | Mach |
| 4,496,342 | A | 1/1985 | Banko |
| 4,583,974 | A | 4/1986 | Kokernak |
| 4,619,655 | A | 10/1986 | Hanker et al. |
| 4,673,296 | A | 6/1987 | Sjogren |
| 4,676,655 | A | 6/1987 | Handler |
| 4,721,390 | A | 1/1988 | Lidgren |
| 4,752,479 | A | 6/1988 | Briggs et al. |
| 4,832,500 | A | 5/1989 | Brunold et al. |
| 4,994,442 | A | 2/1991 | Gil et al. |
| 5,047,030 | A | 9/1991 | Draenert |
| 5,071,040 | A | 12/1991 | Laptewicz, Jr. |
| 5,073,362 | A | 12/1991 | Blaszkiewicz et al. |
| 5,149,368 | A | 9/1992 | Liu et al. |
| 5,168,757 | A | 12/1992 | Rabenau et al. |
| 5,232,024 | A | 8/1993 | Williams |
| 5,252,301 | A | 10/1993 | Nilson et al. |
| 5,262,166 | A | 11/1993 | Liu et al. |
| 5,269,785 | A | 12/1993 | Bonutti |
| 5,281,265 | A | 1/1994 | Liu |
| 5,328,262 | A | 7/1994 | Lidgren et al. |
| 5,328,462 | A | 7/1994 | Fischer |
| 5,342,441 | A | 8/1994 | Mandai et al. |
| 5,360,823 | A | 11/1994 | Griffel et al. |
| 5,403,318 | A | 4/1995 | Boehringer et al. |
| 5,447,711 | A | 9/1995 | Almen et al. |
| 5,462,722 | A | 10/1995 | Liu et al. |
| 5,501,520 | A | 3/1996 | Lidgren et al. |
| 5,549,380 | A | 8/1996 | Lidgren et al. |
| 5,551,778 | A | 9/1996 | Hauke et al. |
| 5,605,885 | A | 2/1997 | Bernton et al. |
| 5,614,206 | A | 3/1997 | Randolph et al. |
| 5,650,108 | A | 7/1997 | Nies et al. |
| 5,665,066 | A | 9/1997 | Fischer |
| 5,681,873 | A | 10/1997 | Norton et al. |
| 5,695,742 | A | 12/1997 | Felder et al. |
| 5,698,186 | A | 12/1997 | Weeks |
| 5,797,873 | A | 8/1998 | Franz et al. |
| 5,829,875 | A | 11/1998 | Hagel et al. |
| 5,837,752 | A | 11/1998 | Shastri et al. |
| 5,842,786 | A | 12/1998 | Solomon |
| 5,866,100 | A | 2/1999 | Tournier et al. |
| 5,871,549 | A | 2/1999 | Jayashankar et al. |
| 5,891,423 | A | 4/1999 | Weeks |
| 5,965,772 | A | 10/1999 | Desantis |
| 5,997,544 | A | 12/1999 | Nies et al. |
| 6,018,094 | A | 1/2000 | Fox |
| 6,018,095 | A | 1/2000 | Lerch et al. |
| 6,062,722 | A | 5/2000 | Lake |
| 6,071,982 | A | 6/2000 | Wise et al. |
| 6,074,358 | A | 6/2000 | Andrew et al. |
| 6,075,067 | A | 6/2000 | Lidgren |
| 6,080,801 | A | 6/2000 | Draenert et al. |
| 6,118,043 | A | 9/2000 | Nies et al. |
| 6,120,174 | A | 9/2000 | Hoag et al. |
| 6,206,957 | B1 | 3/2001 | Driessens et al. |
| 6,231,615 | B1 | 5/2001 | Preissman |
| 6,248,110 | B1 | 6/2001 | Reiley et al. |
| 6,251,139 | B1 | 6/2001 | Lin et al. |
| 6,309,420 | B1 | 10/2001 | Preissman |
| 6,365,218 | B1 | 4/2002 | Borschel et al. |
| 6,367,962 | B1 * | 4/2002 | Mizutani et al. ........... 366/189 |
| 6,431,743 | B1 | 8/2002 | Mizutani et al. |
| 6,440,138 | B1 | 8/2002 | Reiley et al. |
| 6,447,809 | B1 | 9/2002 | Krumhar et al. |
| 6,485,428 | B1 | 11/2002 | Enk |
| 6,488,651 | B1 | 12/2002 | Morris et al. |
| 6,586,009 | B1 | 7/2003 | Lidgren |
| 6,596,904 | B1 | 7/2003 | Dunn et al. |
| 6,689,375 | B1 | 2/2004 | Wahlig et al. |
| 6,706,069 | B2 | 3/2004 | Berger |
| 6,706,273 | B1 | 3/2004 | Roessler |
| 6,716,216 | B1 | 4/2004 | Boucher et al. |
| 6,719,761 | B1 | 4/2004 | Reiley et al. |
| 6,723,334 | B1 | 4/2004 | McGee et al. |
| 6,736,537 | B2 | 5/2004 | Coffeen et al. |
| 6,740,090 | B1 | 5/2004 | Cragg et al. |
| 6,897,339 | B2 | 5/2005 | Turchetta et al. |
| 7,160,306 | B2 | 1/2007 | Matsuzaki et al. |
| 7,393,342 | B2 | 7/2008 | Henniges et al. |
| 7,407,542 | B2 | 8/2008 | Lemaitre et al. |
| 7,417,077 | B2 | 8/2008 | Lidgren et al. |
| 7,524,103 | B2 | 4/2009 | McGill et al. |
| 7,972,630 | B2 | 7/2011 | Lidgren |
| 8,420,127 | B2 | 4/2013 | Lidgren et al. |
| 2001/0012968 | A1 | 8/2001 | Preissman |
| 2001/0051670 | A1 | 12/2001 | Goupil et al. |
| 2002/0055143 | A1 | 5/2002 | Bell et al. |
| 2002/0076378 | A1 | 6/2002 | Wolfe et al. |
| 2002/0101785 | A1 | 8/2002 | Edwards et al. |
| 2002/0156483 | A1 | 10/2002 | Voellmicke et al. |
| 2002/0169506 | A1 | 11/2002 | Matsushima et al. |
| 2003/0018339 | A1 | 1/2003 | Higueras et al. |
| 2003/0028251 | A1 | 2/2003 | Matthews |
| 2003/0040718 | A1 | 2/2003 | Kust et al. |
| 2003/0050702 | A1 | 3/2003 | Berger |
| 2003/0055512 | A1 | 3/2003 | Genin et al. |
| 2003/0109883 | A1 | 6/2003 | Matsuzaki et al. |
| 2003/0161858 | A1 | 8/2003 | Lidgren |
| 2003/0181986 | A1 | 9/2003 | Buchholz |
| 2004/0006347 | A1 | 1/2004 | Sproul |
| 2004/0048947 | A1 | 3/2004 | Lidgren et al. |
| 2004/0049202 | A1 | 3/2004 | Berger |
| 2004/0068234 | A1 | 4/2004 | Martin et al. |
| 2004/0068266 | A1 | 4/2004 | Delmotte |
| 2004/0151751 | A1 | 8/2004 | Cooper |
| 2004/0191897 | A1 | 9/2004 | Muschler |
| 2004/0244651 | A1 | 12/2004 | Lemaitre et al. |
| 2005/0015074 | A1 | 1/2005 | Trombley, III |
| 2005/0023171 | A1 | 2/2005 | Delaney et al. |
| 2005/0105385 | A1 | 5/2005 | McGill et al. |
| 2005/0119746 | A1 | 6/2005 | Lidgren |
| 2005/0128868 | A1 | 6/2005 | Vries |
| 2005/0197629 | A1 | 9/2005 | Conway |
| 2005/0241535 | A1 | 11/2005 | Bohner |
| 2005/0251149 | A1 | 11/2005 | Wenz |
| 2005/0257714 | A1 | 11/2005 | Constantz et al. |
| 2005/0287071 | A1 | 12/2005 | Wenz |
| 2006/0004358 | A1 | 1/2006 | Serhan et al. |
| 2006/0036211 | A1 | 2/2006 | Solsberg et al. |
| 2006/0041033 | A1 | 2/2006 | Bisig et al. |
| 2006/0122621 | A1 | 6/2006 | Truckai et al. |
| 2007/0041906 | A1 | 2/2007 | Lidgren et al. |
| 2007/0161943 | A1 | 7/2007 | Lidgren et al. |
| 2007/0217282 | A1 | 9/2007 | Lidgren et al. |
| 2008/0065088 | A1 | 3/2008 | Hughes et al. |
| 2008/0161752 | A1 | 7/2008 | Rajala et al. |
| 2008/0286331 | A1 | 11/2008 | Lidgren et al. |
| 2008/0318862 | A1 | 12/2008 | Ashman et al. |
| 2009/0018667 | A1 | 1/2009 | Lidgren et al. |
| 2009/0192629 | A1 | 7/2009 | Lidgren et al. |
| 2010/0008181 | A1 | 1/2010 | Lidgren et al. |
| 2010/0249753 | A1 | 9/2010 | Gaisser et al. |

FOREIGN PATENT DOCUMENTS

| | | |
|---|---|---|
| EP | 0 023 992 | 2/1981 |
| EP | 0 109 310 | 5/1984 |
| EP | 0 308 364 | 3/1989 |
| EP | 0 495 284 | 7/1992 |
| EP | 0 639 382 | 2/1995 |

(56) References Cited

FOREIGN PATENT DOCUMENTS

| | | |
|---|---|---|
| EP | 0 657 208 | 6/1995 |
| EP | 0 520 690 | 11/1995 |
| EP | 0 807 432 | 11/1997 |
| EP | 0 950 420 | 10/1999 |
| EP | 1 002 513 | 5/2000 |
| EP | 1 155 704 | 11/2001 |
| EP | 1 208 850 | 5/2002 |
| EP | 1 132 061 | 8/2004 |
| ES | 2 178 556 | 12/2002 |
| GB | 2 239 818 | 7/1991 |
| GB | 2 338 428 | 12/1999 |
| JP | 64-22256 | 1/1989 |
| JP | 64-22257 | 1/1989 |
| JP | 1-139516 | 6/1989 |
| JP | 5-168692 | 7/1993 |
| JP | 5-507862 | 11/1993 |
| JP | 9-502368 | 3/1997 |
| JP | 2935708 | 8/1999 |
| JP | 2000-000295 | 1/2000 |
| JP | 2000-159564 | 6/2000 |
| JP | 2001-106638 | 4/2001 |
| JP | 2001-510078 | 7/2001 |
| JP | 2001-517997 | 10/2001 |
| JP | 2002-058736 | 2/2002 |
| JP | 2002-325831 | 11/2002 |
| JP | 2003-507090 | 2/2003 |
| SE | 8903538 | 4/1991 |
| WO | WO 85/01727 | 4/1985 |
| WO | WO 87/05521 | 9/1987 |
| WO | WO 88/06023 | 8/1988 |
| WO | WO 89/03695 | 5/1989 |
| WO | WO 91/00252 | 1/1991 |
| WO | WO 91/17722 | 11/1991 |
| WO | WO 93/14799 | 8/1993 |
| WO | WO 95/07108 | 3/1995 |
| WO | WO 96/39202 | 12/1996 |
| WO | WO 97/38676 | 10/1997 |
| WO | WO 97/47334 | 12/1997 |
| WO | WO 99/17710 | 4/1999 |
| WO | WO 99/62570 | 12/1999 |
| WO | WO 99/65597 | 12/1999 |
| WO | WO 00/02597 | 1/2000 |
| WO | WO 00/45867 | 8/2000 |
| WO | WO 01/34216 | 5/2001 |
| WO | WO 01/34216 A1 | 5/2001 |
| WO | WO 01/76649 A1 | 10/2001 |
| WO | WO 02/05861 | 1/2002 |
| WO | WO 02/05861 A1 | 1/2002 |
| WO | WO 02/058755 | 8/2002 |
| WO | WO 02/080933 | 10/2002 |
| WO | WO 03/037165 | 5/2003 |
| WO | WO 03/041753 | 5/2003 |
| WO | WO 03/053488 | 7/2003 |
| WO | WO 03/053488 A1 | 7/2003 |
| WO | WO 2004/000374 | 12/2003 |
| WO | WO 2004/002615 | 1/2004 |
| WO | WO 2004/026377 | 4/2004 |
| WO | WO 2004/078223 A1 | 9/2004 |
| WO | WO 2005/099783 A1 | 10/2005 |
| WO | WO 2005/122971 A1 | 12/2005 |
| WO | WO 2006/041365 | 4/2006 |

OTHER PUBLICATIONS

Notice of Allowance in U.S. Appl. No. 10/547,671 dated Dec. 26, 2012; (8 pages).
Office Action in U.S. Appl. No. 10/499,023 dated Jan. 11, 2013; (15 pages).
"Powder (substance)" entry from www.wikipedia.com, <<http://en.wikipedia.org/wiki/Powder_(substance)>> (last visited Dec. 1, 2008) (4 pgs.).
Aebli et al., "Cardiovascular Changes During Multiple Vertebroplasty With and Without Vent-Hole," SPINE (2003) 28(14):1504-1512.
Barbalace, K. "Chemical Database: Calcium sulfate", Environmental Chemistry.com, 2009, 3 pages.
Bohner et al., "Effects of Sulfate Ions on the in Vitro Properties of β-TCP—MCPM-Water Mixtures. Preliminary In Vivo Results," Bioceramics: Materials and Applications, Ceramic Transactions, vol. 48 (1995), pp. 245-259.
Bohner, "New hydraulic cements based on a-tricalcium phosphate-calcium sulfate dihydrate mixtures," Biomaterials (2004) 25, 741-749.
Bohner, M., "Physical and chemical aspects of calcium phosphates used in spinal surgery", Eur. Spine J. (2001) 10:S114-S121.
Cabañas, "Setting Behavior and in Vitro Bioactivity of Hydroxyapatite/Calcium Sulfate Cements," Chem. Mater. (2002) 14, 3550-3555.
Cahn, R.W., ed. "Materials Science and Technology: A Comprehensive Treatment," 1992, vol. 14, VCH, Weinheim, pp. 70-109.
Copending U.S. Appl. No. 10/333,026, filed Jan. 15, 2003 and issued Aug. 26, 2008 as U.S. Patent No. 7,417,077.
Copending Application No. 12/911,198, filed Oct. 25, 2010.
Copending Application No. 12/911,266, filed Oct. 25, 2010.
Damien, C.J. et al., "Investigation of a hydroxyapatite and calcium sulfate composite supplemented with an osteoinductive factor," Student Research Award in the Graduate Degree Candidate Category, 16th Annual Meeting of the Society for Biomaterials, Charleston, SC, May 20-23, 1990; Journal of Biomedical Materials Research, vol. 24, 639-654 (1990).
Database Derwent WPI: Week 198928, Derwent Publications Ltd., JP 1-139516.
Database Derwent WPI: Week 199126, Derwent Publications Ltd., SE 8903538.
Database Derwent WPI: Week 199433, Derwent Publications Ltd., London, GB: AN 1994-269325 & JP 61-99623 (Lion Corp. et al.), Jul. 19, 1994.
Database Derwent WPI: Week 199734, Derwent Publications Ltd., EP 0 807 432.
Database Derwent WPI: Week 200138, Derwent Publications Ltd., WO 2001/34216.
De Robertis et al., "Solubility of some calcium-carboxylic ligand complexes in aqueous solution," Talanta (1995) 42:1651-1662.
Elliott, J. C. "General Chemistry of the Calcium Orthophosphates," in Structure and Chemistry of the Apatites and Other Calcium Orthophosphates, 1994, Elsevier: Netherlands, Chapter 1, pp. 1-9.
English language abstract of JP 2000-000295.
English language abstract of JP 2001-106638.
English language abstract of JP 2001-517997; (1 page).
English language abstract of JP 2002-325831; (1 page).
English language abstract of JP 2935708; (1 page).
English language abstract of JP 5-168692.
English language abstract of JP 5-507862.
English language translation of Japanese Office Action dated Jun. 2, 2009 in Japanese Application No. 2003-554244 related to U.S. Appl. No. 10/499,023.
English language translation of Japanese Office Action dated May 26, 2010 in Japanese Application No. 2006-539432 related to U.S. Appl. No. 10/578,734; (12 pages).
English language translation of Japanese Office Action dated Sep. 9, 2010 in Japanese Application No. 2006-507949 related to U.S. Appl. No. 10/547,671; (4 pages).
English language translation of Japanese Patent Application No. 2002-511792.
English language translation of JP 64-22256.
English language translation of JP 64-22257.
English language Abstract of EP 0 657 208.
English language translation of ES 2 178 556, "Calcium sulfate cement capable of controlled biodegradation," (10 pgs.).
English language translation of JP 1-139516.
English-language translation of SE 8903538, "Implant material and method for the manufacture thereof," Bioapatite AB.
Engqvist et al., "Chemical Stability of a Novel Injectable Bioceramic for Stabilisation of Vertebral Compression Fractures," Trends Biomater. Artif. Organs (2008) 21(2):98-106.

(56) References Cited

OTHER PUBLICATIONS

Eromosele et al., "Characterization and viscosity parameters of seed oils from wild plants", Science Direct: Bioresource Technology, 2002, 7 pages.
Ima-Nirwana et al., "Palm vitamin E improves bone metabolism and survival rate in thyrotoxic rats," Gen. Pharmacol. (1999) 32:621-626.
International Preliminary Examination Report for PCT/SE01/00789 dated Jan. 11, 2002, related to U.S. Appl. No. 10/257,561.
International Preliminary Examination Report for PCT/SE01/01627 dated Oct. 14, 2002, related to U.S. Appl. No. 10/333,026.
International Preliminary Examination Report for PCT/SE02/02428 dated Mar. 16, 2004, related to U.S. Appl. No. 10/499,023.
International Preliminary Examination Report for PCT/SE2004/000328 dated Aug. 30, 2005, related to U.S. Appl. No. 10/547,671.
International Preliminary Report on Patentability for PCT/SE2004/001626 dated Feb. 13, 2006.
International Preliminary Report on Patentability for PCT/SE2005/000932 dated Dec. 28, 2006.
International Search Report for PCT/SE01/00789 dated Jul. 9, 2001, related to U.S. Appl. No. 10/257,561.
International Search Report for PCT/SE01/01627 dated Dec. 18, 2001, related to U.S. Appl. No. 10/333,026.
International Search Report for PCT/SE02/02428 dated Apr. 4, 2003, related to U.S. Appl. No. 10/499,023.
International Search Report for PCT/SE2004/000328 dated Jun. 8, 2004, related to U.S. Appl. No. 10/547,671.
International Search Report for PCT/SE2004/001626 dated Feb. 28, 2005.
International Search Report for PCT/SE2005/000932 dated Oct. 10, 2005.
Kirby et al., "Acute Bronchospasm Due to Exposure to Polymethylmethacrylate Vapors during Percutaneous Vertebroplasty," AJR (2003) 180:543-544.
Koessler et al., "Fat and Bone Marrow Embolism During Percutaneous Vertebroplasty," Anesth. Analg. (2003) 97:293-294.
Komath et al., "On the development of an apatic calcium phosphate bone cement," Bull. Mater. Sci (2000) 23(2):135-140.
Lidgren, "Bone Substitutes," Karger Gazette (2002) 65:1-4.
Machine Translation of JP 2002-058736; (15 pages).
Mirtchi et al., "Calcium phosphate cements: action of setting regulators on the properties of the β-tricalcium phosphate-monocalcium phosphate cements," Biomaterials (1989), 10(9), pp. 634-638.
Nilsson et al., "Biodegradation and biocompatability of a calcium sulphate-hydroxyapatite bone substitute," J. of Bone & Joint Surgery (Br) (2004) 86-B:120-125.
Nilsson et al., "Characterization of a novel calcium phosphate/sulphate bone cement," J. Biomedical Materials Research (2002) 61(4), 600-607.
Nilsson et al., "New Perspectives of Bioactives Calcium Phosphate Cements for Biomedical Applications," Research Centre in Biomedical Engineering, Dept. of Material Science and Metallurgy, Universitat Politecnica de Catalunya, Avda, Diagonal 647k Barcelona, E-08028, Spain, pp. 95-99, Nov. 2000.
Nilsson et al., "The Effect of Aging an Injectable Bone Graft Substitute in Simulated Body Fluid," Key Engineering Materials, vols. 240-242 (2003), pp. 403-406.
Notice of Allowance in copending U.S. Appl. No. 10/333,026 dated Apr. 25, 2008.
Notice of Allowance in copending U.S. Appl. No. 10/257,561 dated Feb. 23, 2011; (8 pages).
Notice of Allowance in copending Application No. 10/578,734 dated Dec. 29, 2010; (6 pages).
Notice of Allowance in copending Application No. 10/578,734 dated Jul. 27, 2010; (27 pages).
Notice of Allowance in copending U.S. Appl. No. 11/587,313 dated Jan. 26, 2011; (4 pages).
Notice of Allowance in copending U.S. Appl. No. 12/585,194 dated Mar. 22, 2012; (8 pages).
Office Action and English language translation thereof for Japanese Patent Application 2001-574164, corresponding to U.S. Appl. No. 10/257,561 dated Feb. 2, 2011; (10 pages).
Office Action in copending U.S. Appl. No. 10/257,561 dated Apr. 27, 2010; (12 pages).
Office Action in copending U.S. Appl. No. 10/257,561 dated Apr. 3, 2009.
Office Action in copending U.S. Appl. No. 10/257,561 dated Jul. 2, 2008.
Office Action in copending U.S. Appl. No. 10/257,561 dated Mar. 28, 2007.
Office Action in copending U.S. Appl. No. 10/257,561 dated Nov. 10, 2009.
Office Action in copending U.S. Appl. No. 10/257,561 dated Oct. 15, 2007.
Office Action in copending U.S. Appl. No. 10/257,561 dated Sep. 5, 2006.
Office Action in copending U.S. Appl. No. 10/333,026 dated Oct. 10, 2007.
Office Action in copending U.S. Appl. No. 10/333,026 dated Oct. 31, 2006.
Office Action in copending U.S. Appl. No. 10/333,026 dated Mar. 21, 2006.
Office Action in copending U.S. Appl. No. 10/499,023 dated Apr. 17, 2009.
Office Action in copending U.S. Appl. No. 10/499,023 dated Jul. 22, 2008.
Office Action in copending U.S. Appl. No. 10/499,023 dated Jun. 10, 2010 (21 pages).
Office Action in copending U.S. Appl. No. 10/499,023 dated Oct. 4, 2007.
Office Action in copending U.S. Appl. No. 10/499,023 dated Sep. 9, 2009.
Office Action in copending U.S. Appl. No. 10/547,671 dated Aug. 16, 2010.
Office Action in copending U.S. Appl. No. 10/547,671 dated Aug. 23, 2011, 14 pages.
Office Action in copending U.S. Appl. No. 10/547,671 dated Aug. 5, 2009.
Office Action in copending U.S. Appl. No. 10/547,671 dated May 29, 2012, 10 pages.
Office Action in copending U.S. Appl. No. 10/547,671 dated May 5, 2010.
Office Action in copending U.S. Appl. No. 10/578,734 dated Oct. 26, 2009.
Office Action in copending U.S. Appl. No. 11/587,313 dated Jun. 18, 2010; (22 pages).
Office Action in copending U.S. Appl. No. 12/122,873 dated Feb. 27, 2012; (11 pages).
Office Action in copending U.S. Appl. No. 12/122,873 dated Jun. 19, 2009.
Office Action in copending U.S. Appl. No. 12/122,873 dated Mar. 19, 2010; (8 pages).
Office Action in copending U.S. Appl. No. 12/122,873 dated Oct. 29, 2009.
Office Action in copending U.S. Appl. No. 12/122,873 dated Sep. 8, 2010; (8 pages).
Office Action in copending U.S. Appl. No. 12/219,542 dated Jan. 11, 2010.
Office Action in copending U.S. Appl. No. 12/219,542 dated Jun. 19, 2009.
Office Action in copending U.S. Appl. No. 12/219,542 dated Jun. 25, 2010; (10 pages).
Office Action in copending U.S. Appl. No. 12/219,542 dated Mar. 1, 2012; (10 pages).
Office Action in copending U.S. Appl. No. 12/219,542 dated Oct. 18, 2010; (9 pages).
Office Action in copending U.S. Appl. No. 12/219,543 dated Feb. 27, 2012; (8 pages).
Office Action in copending U.S. Appl. No. 12/219,543 dated Mar. 19, 2010; (7 pages).
Office Action in copending U.S. Appl. No. 12/219,543 dated Sep. 8, 2010; (7 pages).

(56) References Cited

OTHER PUBLICATIONS

Office Action in copending U.S. Appl. No. 12/585,194 dated Aug. 11, 2011, (15 pages).

Parsons, John R., et al., "Osteoconductive Composite Grouts for Orthopedic Use", pp. 190-207.

Starling, S., "EFSA Says Clacium Sulphate Safe in Supplements", 2008, Nutraingredients.com, 4 pages.

Supplemental Notice of Allowance in copending U.S. Appl. No. 10/578,734 dated Sep. 17, 2010; (5 pages).

Technical Specification, Calcium Suolfate Hemihydrate Food Grade, 2009, 1 page.

Written Opinion of the International Searching Authority for PCT/SE2004/001626 dated Feb. 28, 2005.

Written Opinion of the International Searching Authority for PCT/SE2005/000932 dated Oct. 10, 2005.

English language translation of Japanese Office Action mailed Jun. 1, 2010, in Japanese Application No. 2006-539432.

English language translation of Japanese Office Action, dated Oct. 3, 2011, in Japanese Patent Application No. 2002-511972.

Examiner Interview Summary in U.S. Appl. No. 13/022,771 dated Apr. 3, 2013.

Gitelis, S. et al., "The treatment of chronic osteomyelitis with a biodegradable antibiotic-impregnated implant," *J. Orthopaedic Surgery* (2002) 10(1): 53-60.

Karr, J. C., "Management of a Diabetic Patient Presenting With Forefoot Osteomyelitis: The Use of Cerament Bone Void Filler Impregnated With Vancomycin—An Off Label Use," *J. Diabetic Foot Complications* (2009) 1(4): 94-100.

Lei et al., "Mechanical properties of calcium sulphate/hydroxyapatite cement," *Bio-Medical Materials and Engineering* (2006)16: 423-428.

Notice of Allowance in U.S. Appl. No. 10/499,023, dated Jul. 17, 2013.

Office Action in U.S. Appl. No. 13/022,771, dated Aug. 8, 2013.
Office Action in U.S. Appl. No. 13/022,771, dated Nov. 14, 2012.
Office Action in U.S. Appl. No. 13/799,959, dated Jul. 16, 2013.
Office Action in U.S. Appl. No. 13/613,563, dated May 14, 2013.

Richelsoph, K. C. et al., "Elution Behavior of Daptomycin-loaded Calcium Sulfate Pellets," *Clin. Orthopaedics and Related Res.* (2007) 461: 68-73.

Singh, N. B. et al., "Calcium Sulphate Hemihydrate Hydration Leading to Gypsum Crystallization," *Prog. Crystal Growth & Characterization of Materials* (2007) 53: 57-77.

\* cited by examiner

DEVICE FOR PRODUCING A HARDENABLE MASS

This is a division of application Ser. No. 12/585,194, filed Sep. 8, 2009 now U.S. Pat. No. 8,297,831, which is a division of application Ser. No. 11/587,313, filed Oct. 23, 2006, now U.S. Pat. No. 7,938,572, which is a 371 of PCT/SE05/00932, filed Jun. 17, 2005, which claims priority to Swedish patent application no. 0401604-4, filed Jun. 22, 2004.

FIELD

The present invention relates to a device for producing a hardenable mass, preferably a bone substitute and/or bone reinforcing material or bone cement or a similar material, wherein a mixing container has a mixing space in which at least one powder and at least one liquid component are mixed to provide the hardenable mass. A piston means is provided in the mixing space of the mixing container, which piston means can be retained relative to the mixing container and be released such that it can move in relation thereto in a direction towards at least one opening through which mixed mass can pass out of the mixing container, wherein at least one means which is rotatable relative to the mixing container cooperates with the piston means for, in a retaining position, retaining said piston means relative to the mixing container and, by rotation to a release position, releasing the piston means such that said piston means can move towards the opening.

Osteoporosis is rapidly increasing, particularly in the industrialized countries. One reckons that about 50% of all women will suffer from fractures due to osteoporosis. The major part of these fractures are found on older people and lead to increased mortality, invalidity and huge social costs. Vertebroplasty is a percutaneous injection of bone cement into a vertebra in order to alleviate pain in a compression fracture caused by osteoporosis. Vertebroplasty was performed for the first time in France in 1984 and ten years later in the USA. Kyphoplasty means balloon expansion in a collapsed vertebra for, if possible, reducing the risk for further collapse of the vertebra and provide a cavity which is filled with bone cement. Kyphoplasty is regarded as experimental in Europe, but has recently been approved by the FDA for treatment of pathological fractures together with polymeric bone cements. The drawback with kyphoplasty is that this method requires general anaesthesia. Vertebroplasty however, can be performed in a surgery in fluoroscopy while administering sedatives and analgesics. Both methods give satisfactory pain relief in more than 75% of the cases. Early treatment of vertebra compression with vertebroplasty is still discussed even if satisfactory pain relief can be provided. It is recommended to wait at least six weeks before vertebroplasty is performed. While waiting, pain killing treatment is tested. Early treatment with vertebroplasty however, can be considered if there is a risk for complications causing immobilization or if the pain is severe. A principal object with vertebroplasty is except pain relief to prevent further collapse of vertebra. For identifying fractures, MR can be used besides common X-ray, said MR also showing oedema in the bone marrow and fracture gaps in the vertebra.

Vertebroplasty is performed with the patient lying on his or her stomach or on the side during intraveneous sedation and pain relief and under control by a physician. During additional local anesthesia, a needle is inserted into a mandrine in the vertebra during fluoroscopy via a transpedicular or posteolateral inlet. The needle shall be positioned in the centre line, preferably in the fore or anterior part of the vertebra. Then, injection of cement is carried through. Another needle is often necessary for symmetric filling of the vertebra. The injection of cement is carefully supervised via TV-fluoroscopy and if leakage occurs outside the limits of the vertebra, the injection is interrupted. The required volume for adequate pain relief is small, about 2-3 ml. If larger volumes are used, the risk increases that cement will leak out, as is the risk that bone marrow will spread into the circulation system during injection. The injection requires technical knowledge and training. Almost all substantial complications depend on leakage of cement to the spinal canal or through the injection site. In more than 20% there is an asymptomatic leakage of cement into paraspinal soft parts or the lumbar venous system.

BACKGROUND

Devices for producing and discharging masses for the abovementioned and similar purposes are already known from U.S. Pat. No. 4,676,655, GB 2239818, WO 2004/026377, WO 99/65597, EP 0657208 and WO 2004/002615. Prior art devices according to these publications however, are no simple devices permitting simple handling in connection with vertebroplasty or similar.

SUMMARY

The object of the present invention is to provide a simple device permitting simple handling in connection with vertebroplasty and similar. This is arrived at by providing the device defined above with the characterizing features of subsequent claim 1.

The significance of using a device permitting utterly simple handling during, inter alia, vertebroplasty and which relieves the surgeon from several technical measures for moving cement from e.g. mixing in a bowl to a smaller syringe, is of the utmost importance. Simple handling regarding mixing as well as discharge of cement, is important. Closed systems are, if polymethylmethacrylate shall be used, necessary for hygienic reasons in order not to release monomer into the surrounding air. The possibility of having prepacked systems permitting sterilization together with closed transfer to smaller syringes for improved control during injection, is obvious. Today, we have no simple and efficient mixing and discharge equipment complying with these demands. The equipment must be able to manage mixing of polymeric as well as ceramic materials in well-balanced volumes and to stop the injection if leakage occurs. The invention comprises in this regard a number of novelties.

BRIEF DESCRIPTION OF THE DRAWINGS

The invention will be further described below with reference to the accompanying drawings, in which.

DETAILED DESCRIPTION

Figure 1:
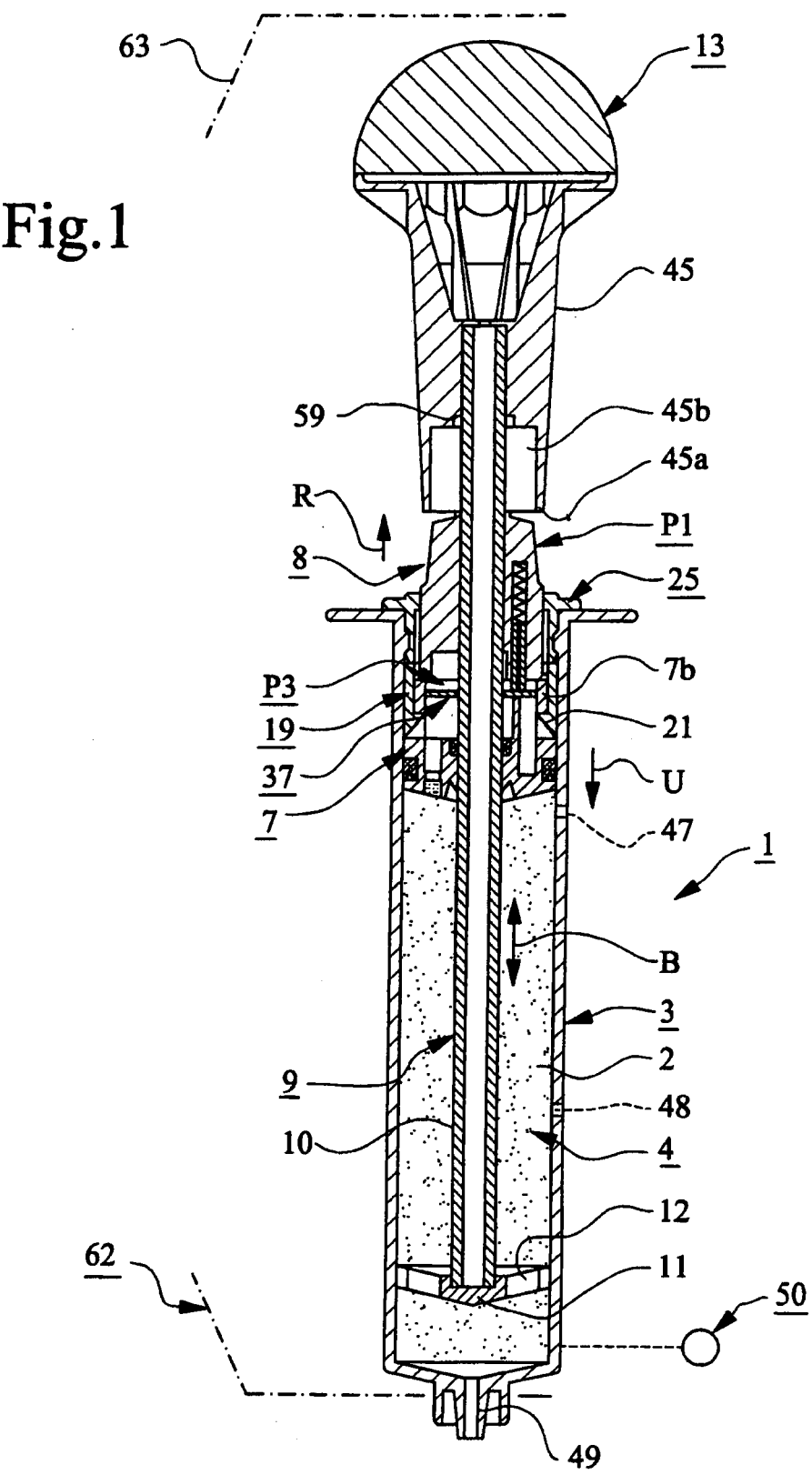
FIG. 1 is a longitudinal section through the device according to the invention during a mixing step.

The device 1 illustrated in the drawings is adapted for producing a hardenable mass 2 such as bone substitute and/or bone reinforcing material or bone cement or similar material. This mass 2 shall be fed and/or sucked out of the device 1 and comprises a mixing container 3 of e.g. cylindrical shape. The mixing container 3 defines a mixing space 4 in which at least one powder component 5 and at least one liquid component 6 are mixed to produce the hardenable mass 2.

In the mixing space 4 there is provided a piston means 7 which is adapted to be retained relative to the mixing container 3 during a mixing step and thereafter released such that it can move in the mixing space 4 relative to the mixing container 3. In order to release the piston means 7 there is provided a rotatable means 8 which in a retaining position P1 retains the piston means 7 relative to the mixing container 3 and which by rotation from the retaining position P1 to a release position P2 can be released relative to the mixing container 3, whereby the piston means 7 can move in the mixing space 4. The piston means 7 and the rotatable means 8 are preferably directly or indirectly interconnected.

The device 1 preferably but not necessarily comprises a mixing means 9 which is provided for mixing the powder and liquid components 5, 6 with each other until the hardenable mass 2 has been produced. Then, the mass 2 can be stirred with the mixing means 9 if this is appropriate or necessary. The mixing means 9 may comprise an elongated member 10, e.g. a hollow or solid rod, which extends into the mixing space 4 and which at an inner end within the mixing space 4 has a mixing disc 11 with axial holes 12 passing through said disc. At an outer end outside the mixing space 4, the elongated member 10 is provided with an operating handle 13 for operating the mixing means 9.

The mixing/stirring can be carried through in a known manner by moving the mixing means 9 back and forth in the mixing space 4 and preferably also rotating it relative to said mixing space 4.

The piston means 7 preferably has an axial hole 14 extending therethrough and by means of which the elongated member 10 of the mixing means 9 extends into the mixing space 4. The elongated member 10 cooperates with the piston means 7 through one or more sealing rings 15 or similar, such that a sealing is provided between said members. The elongated member 10 and the hole 14 of the piston means 7 are adapted to each other such that said elongated member 10 can be moved and rotated relative to the piston means 7.

At least one outer sealing 16 or similar is provided on the piston means 7 for cooperation with the inner side of the mixing container 3 such that a sealing is defined between the piston means 7 and said inner side. The outer sealing ring 16 is preferably designed such that it removes mass 2 which deposits on the inner side of the mixing container 3 when it moves in the mixing space 4.

The piston means 7 may also have an opening 17 with at least one filter 18. The opening 17 is adapted to let out gases from the mixing space 4 and the filter 18 is adapted to prevent the components 5 and/or 6 and the mixed mass 2 from forcing its way out of the mixing space 4 through the opening 17.

A rotary-movement preventing member 19 is provided on the piston means 7. This member 19 is annular and includes two axially provided hook portions 20, 21 which can be inserted into grooves 22, 23 in the piston means 7 and hooked onto two shoulders 7a, 7b thereon in a radial direction. By means of this positioning, the rotary-movement preventing member 19 is attached to the piston means 7 and can not rotate relative to said means.

The rotary-movement preventing member 19 further includes an axially provided flange 24 which is adapted to cooperate with a bracket 25 in order to prevent rotation of the rotary-movement preventing member 19 and thus, the piston means 7, relative to the bracket 25 such that the mixing means 9 is rotated relative to the piston means 7 for mixing of the powder and liquid components 5, 6. The bracket 25 has a cylindrical member 27 with a hole 28 into which the rotatable means 8 can be inserted and through which said rotatable means can move when it is set in a release position P2. The cylindrical member 27 of the bracket 25 may have an annular snap-in portion 29 which can be threaded into one or more locking portions 30 which are located at the inner side of the mixing container 3 and which allow the bracket 25 to be attached to the mixing container 3 by a snap-in closure. Alternatively or in combination with said snap-in portion 29, the bracket 25 may have a number of radially projecting members 33, 34 which can be attached to a radially outwards directed flange 35 on the mixing container 3 by a snap-in closure such that the bracket 25 can not rotate relative to said container.

The rotatable means 8 has a through hole 8a through which the elongated member 10 of the mixing means 9 extends such that said elongated member 10 is movable relative to the rotatable means 8 and vice versa.

The rotatable means 8 has a first flange 36 or a corresponding member which in relation to the direction U extends radially outwards from the rotatable means 8 towards a discharge opening 49 through which the mass 2 shall pass out of the mixing container 3. Said first flange 36 surrounds a part of the periphery of the rotatable means 8.

The hole 28 of the bracket 25 has a second flange 31a or a corresponding second member which relative to the direction U is directed radially into the hole 28. This second flange 31a extends along a part of the periphery of the hole 28. A section 31b or a corresponding third part of the hole 28 lacks said flange 31a and is designed such that the first flange 36 of the rotatable means 8 can pass therethrough, whereby the entire rotatable means 8 can be brought to pass through the hole 28 when the first flange 36 and the section 31b cooperate.

When the rotatable means 8 is set in the retaining position P1 (FIG. 1), then the first and second flanges 36 and 31a cooperate and prevent the rotatable means 8 from moving relative to the bracket 25 in direction U, while the mixing means 9 can move and be brought to perform mixing movements for mixing the powder and liquid components in the mixing space 4.

Figure 2:
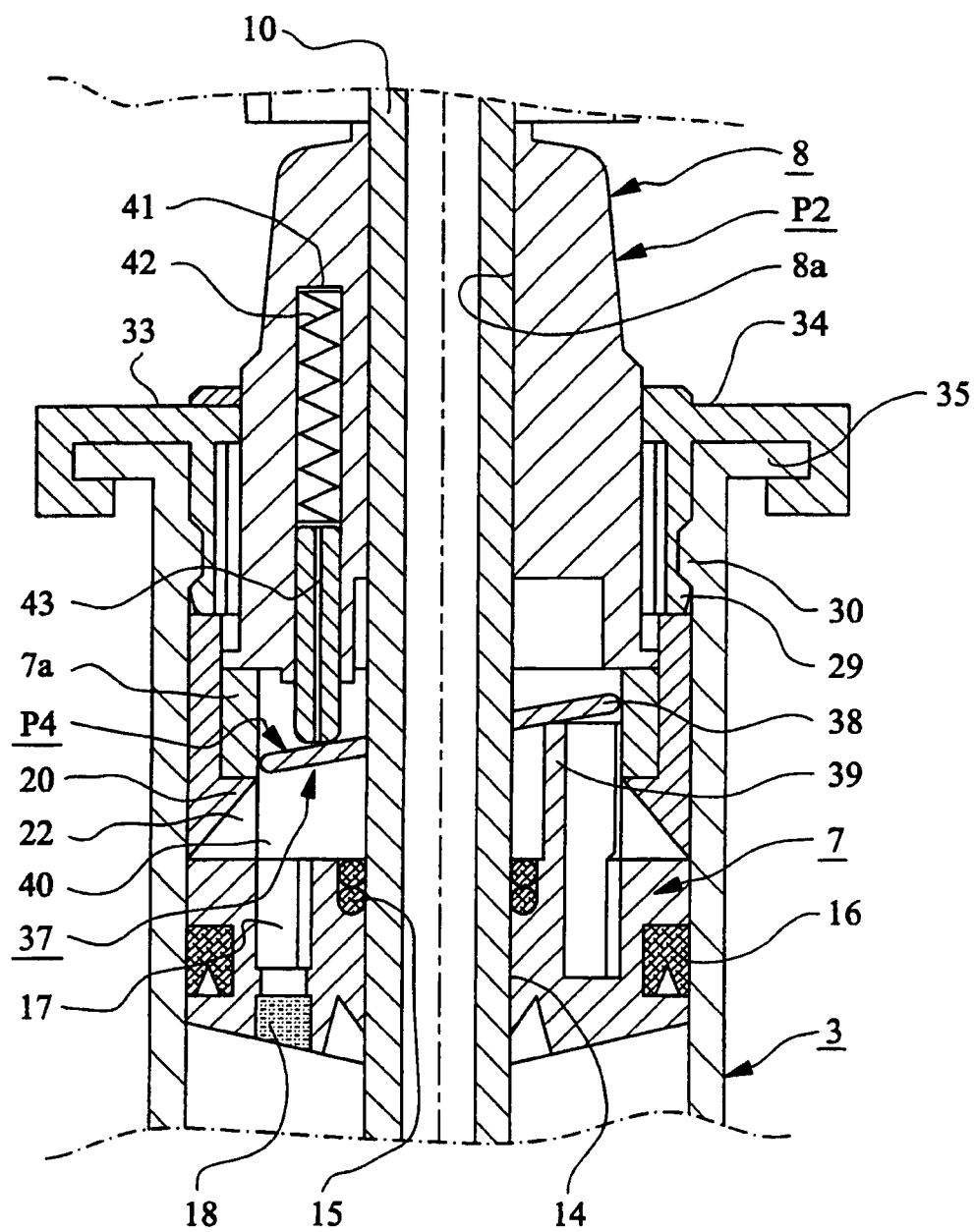
FIG. 2 is an enlarged sectional view of a part of the device of FIG. 1 and shows a mixing means interconnected with a discharge means.
Figure 3:
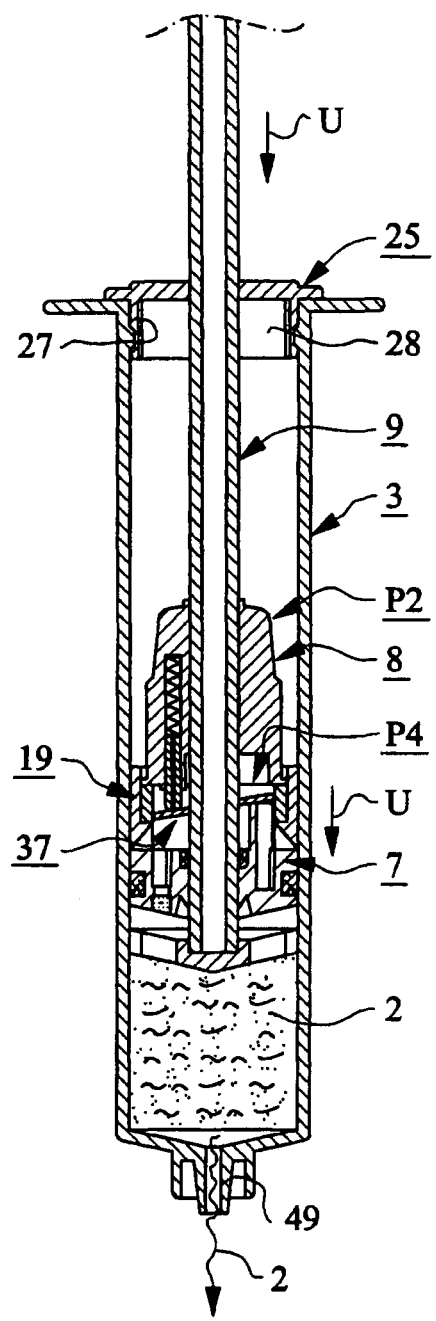
FIG. 3 is a section through the device of FIG. 1 during a discharge step.
Figure 7:
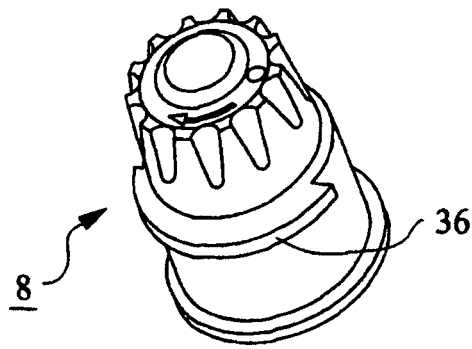
FIG. 7 is a perspective view of a rotatable means forming part of the device of FIG. 1.
Figure 4:
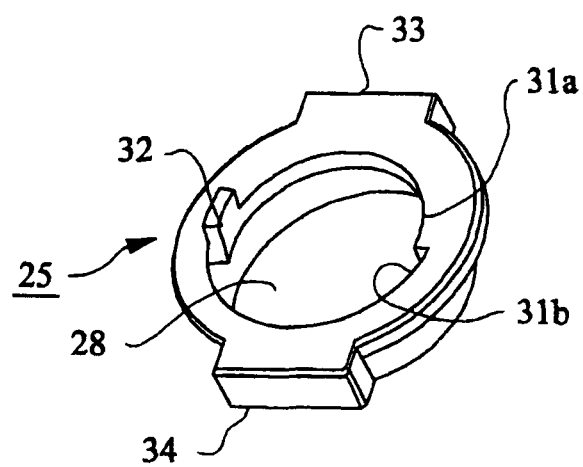
FIG. 4 is a perspective view of a bracket forming part of the device of FIG. 1.
Figure 6:
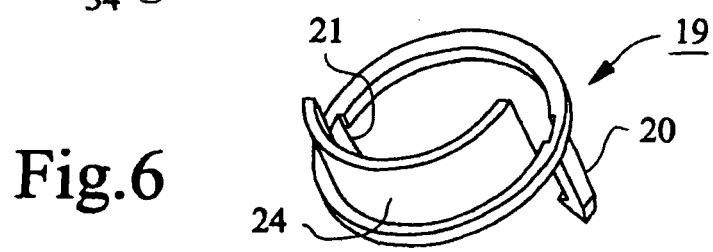
FIG. 6 is a perspective view of a rotary-movement preventing member forming part of the device of FIG. 1.
Figure 5:
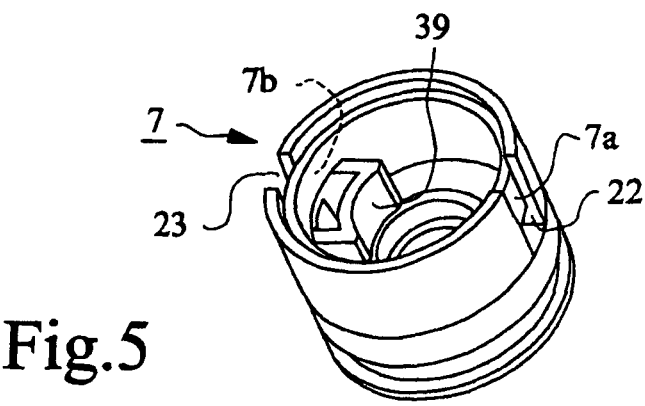
FIG. 5 is a perspective view of a discharge piston forming part of the device of FIG. 1.
Figure 8:
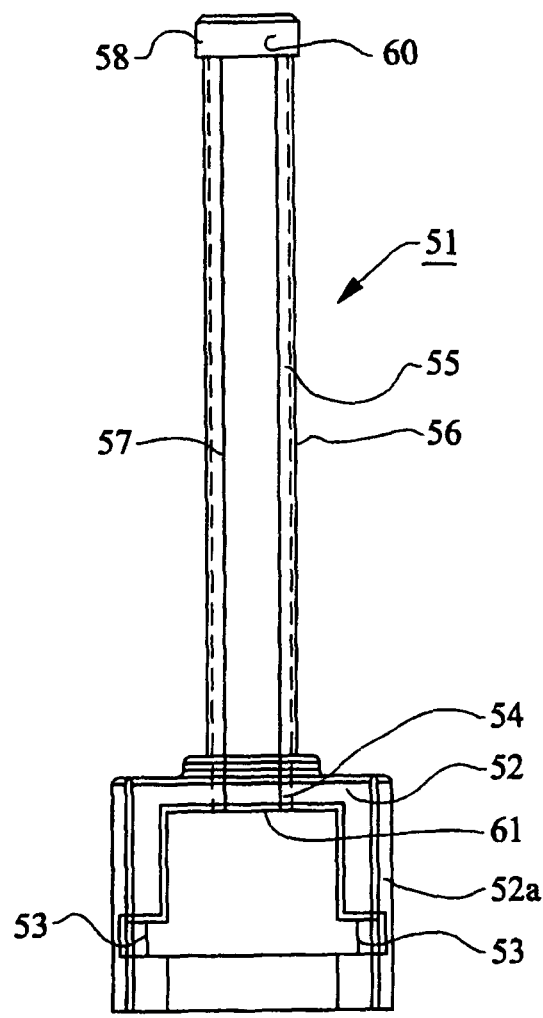
FIG. 8 is a side view of a screw mechanism for use at the device of FIG. 1.

The rotatable means 8 can be brought to its release position P2 (FIG. 2) by rotating it 180° relative to the bracket 25 from its retaining position P1 and this rotary movement can be limited by bringing the first flange 36 thereof to engage or abut a rotary stop 32. Thereby, the first flange 36 of the rotary means 8 will be disengaged from the cooperation with the second flange 31*a* of the bracket 25 and it can instead cooperate with the section 31*b* of the bracket 25 such that the rotatable means 8 and thus, the piston means 7, can move and be displaced in direction U in relation thereto and thus, relative to the mixing container 3.

The piston means 7 is prevented from rotating relative to the bracket 25 by the flange 24 of the rotary-movement preventing member 19 engaging or gripping preferably into the section 31*b* of the bracket 25 when the rotatable means 8 retains the piston means 7 at the bracket 25.

The rotatable means 8 cooperates preferably with a coupling device 37 which is provided to interconnect the piston means 7 and the elongated member 10 of the mixing means 9 such that the piston means 7 (and the rotatable means 8 provided thereby) can be displaced in axial direction U relative to the mixing container 3 by means of the mixing means 9 for discharge of mixed mass 2 from the mixing space 4. The coupling device 37 is located between the rotatable means 8 and the piston means 7 and it is preferably provided to be operated by the rotatable means 8 such that it connects the piston means 7 to the elongated member 10 while simultaneously the rotatable means 8 is rotated from its retaining position P1 to its release position P2. To this end, the coupling device 37 may comprise a coupling means 38, e.g. a washer, which is threaded onto the elongated member 10 and which is located between the piston means 7 and the rotatable means 8. The piston means 7 has a support member 39 which is axially directed towards the rotatable means 8 and located on one side of the elongated member 10, while there is a free space 40 on the other side of the elongated member 10. The rotatable means 8 has an axially directed bore 41, the rear parts of which are provided with a helical spring 42 or a similar resilient element and the fore parts with a pin 43 which projects out of the bore 41.

When the rotatable means 8 is set in its retaining position P1, the bore 41 with the helical spring 42 is located on the same side of the elongated member 10 and the helical spring thereby presses the coupling means 38 against the support member 39 such that said coupling means 38 is held in a neutral position P3 in which it is held against the support member 39 and permits displacement of the elongated member 10 of the mixing means 9 in opposite axial mixing directions B, whereby the powder and liquid components 5, 6 can be mixed in the mixing space 4 with the mixing means 9 while the piston means 7 is retained relative to the mixing container 3.

When the rotatable means 8 is rotated 180° to its release position P2, the bore 41 and the helical spring 42 will also move 180° relative to the support member 39 and the helical spring 42 will thereby press or push the coupling means 38 into the space 40, which means that the coupling means 38 is tilted relative to the elongated member 10 and is brought to a coupling position P4 in which the coupling means 38 is fastened to the elongated member 10. Hereby, the piston means 7 is connected to the mixing means 9 such that the piston means 7 can be displaced in the direction U by said mixing means 9.

Preferably, the coupling device 37 is designed such that it, after said interconnection of the mixing means 9 and the piston means 7, permits release of the mixing means 9 relative to the piston means 7 if said mixing means 9 is pulled in the return direction R relative to the piston means 7.

On the operating handle 13 and/or on the elongated member 10 there may be provided an outer member 45 with an open end portion 45*a* and such a cavity or depression 45*b* within the end portion 45*a* that said end portion will engage or abut the mixing container 3 when the mixing means 9 is displaced in axial direction towards the mixing container 3 and rotated relative to said container during mixing. Hereby, it is prevented that said rotation of the mixing means 9 is transferred to the rotatable means 8.

The bracket 25 is preferably provided to prevent the piston means 7 and the mixing means 9 from being pulled apart from the mixing container 3.

Since the rotatable means 8 can move together with the piston means 7 in the mixing space 4 of the mixing container 3, it is ensured that the device 1 will be simple and that it provides for a simple and quick handling when mixing of the powder and liquid components 5, 6 has been performed and the mixed mass 2 shall be discharged. To this end, it is only necessary to rotate the rotatable means 8 from its retaining position P1 to the release position P2, whereafter it is possible to displace the piston means 7 by means of the mixing means 9 in the direction U for discharge of the mass 2 from the mixing space 4.

As an alternative to the opening 17, at least one opening 47 can be provided in the side of the mixing container 3 adjacent the piston means 7 when said piston means is retained by the bracket 25. Since the opening 47 is located adjacent the piston means 7, it is closed when the piston means 7 starts to move in the direction U and after further movement of the piston means 7, it will be located behind said piston means, which means that only gas and no mass 2 can be pressed out through the opening 47.

As an alternative to said openings, there may be at least one opening 48 in the side of the mixing container 3 about half the way between the piston means 7, when retained by the bracket 25, and a discharge opening 49 which is provided in the mixing container 3 for discharge of the mass 2 from said container. The opening 48 may be closable when necessary.

The abovementioned opening 17 or openings 47 or 48 permit gas to be pressed out of the mixing space 4 when e.g. the liquid component 6 is injected into said space. Since gas hereby can be pressed out, injection of the liquid component 6 is facilitated. Due to its location, the opening 48 permits gas which is entrapped in the mass 2 to be pressed out of or escape from said mass during discharge thereof.

At least one vacuum generating device can be provided to generate a vacuum in the mixing space 4 for various purposes, preferably for facilitating quick suction of the liquid component 6 to and distribution thereof in the powder component 5 and/or e.g. for sucking out toxic gases therefrom, which are generated during mixing of the powder and liquid components 5, 6. In this case, there may be no openings which let air into the mixing container 3, but said container must be sealed.

In order to generate a vacuum in the mixing space 4 for e.g. sucking out toxic gases, there may be a first vacuum generating device 50 which at a suitable location can be connected to the mixing container 3. Such a first vacuum generating device 50 is schematically illustrated in FIG. 1.

For discharge, the mixing means 9 can be subjected to linear forces such that said mixing means 9 and the piston means 7 are displaced linearly relative to the mixing container 3. Alternatively, the mixing means 9 can be displaced linearly by influence from a screw device 51.

The screw device 51 e.g. includes a nut-like member 52 which has a laterally open fork-like member 52*a* with laterally open grooves 53 permitting sideways threading of the nut-like member 52 onto the flange 35 of the mixing container 3 such that said member 52 is stuck on the mixing container 3.

The nut-like member 52 is provided with a tapped hole 54 for a screw-like member 55 with outer threads 56 which mesh with the threads in the tapped hole 54 of the nut-like member 52. The screw-like member 55 may be a pipe member with a multi-side nut 58 and the pipe member may have a longitudinal slit 57 which is open in a lateral direction and the multi-side nut 58 may have an open side 60 such that the screw-like member 55 and the multi-side nut 58 can be threaded onto the elongated member 10 of the mixing means 9. The multi-side nut 58 is adapted to fit into a corresponding multi-side hole 59 in the outer member 45 or any other member on or of the operating handle 13.

Due to the abovementioned embodiment of the screw device 51, said device can be non-rotatably located on the mixing container 3 and since the multi-side nut 58 can be inserted into the hole 59, the screw-like member 55 may, by means of the operating handle 13, be screwed into the nut-like member 52 via e.g. the outer member 45, whereby the end portion 61 of the screw-like member 55 is brought in contact with the rotatable means 8 and can impart dis-charge forces in the direction U to the rotatable means 8 and through said rotatable means to the piston means 7.

The piston means 7 can be moved in the direction U either by manually pressing the operating handle 13 or rotating it and transfer the rotary movement by means of the screw device 51. If great forces are required for discharging the mass 2 from the mixing space 4, one can use a gun-like discharge device 62 or a similar device as is schematically indicated in FIG. 1. The mixing container 3 is positioned therein such that a pressure means 63 can cooperate with the mixing means 9 or directly with the piston means 7 if there is no mixing means. The pressure means 63 is operated by a manually depressable trigger which can move the pressure means 63 stepwise such that said pressure means with force press the mixing means 9 and/or the piston means 7 forward in the direction U.

Figure 9:
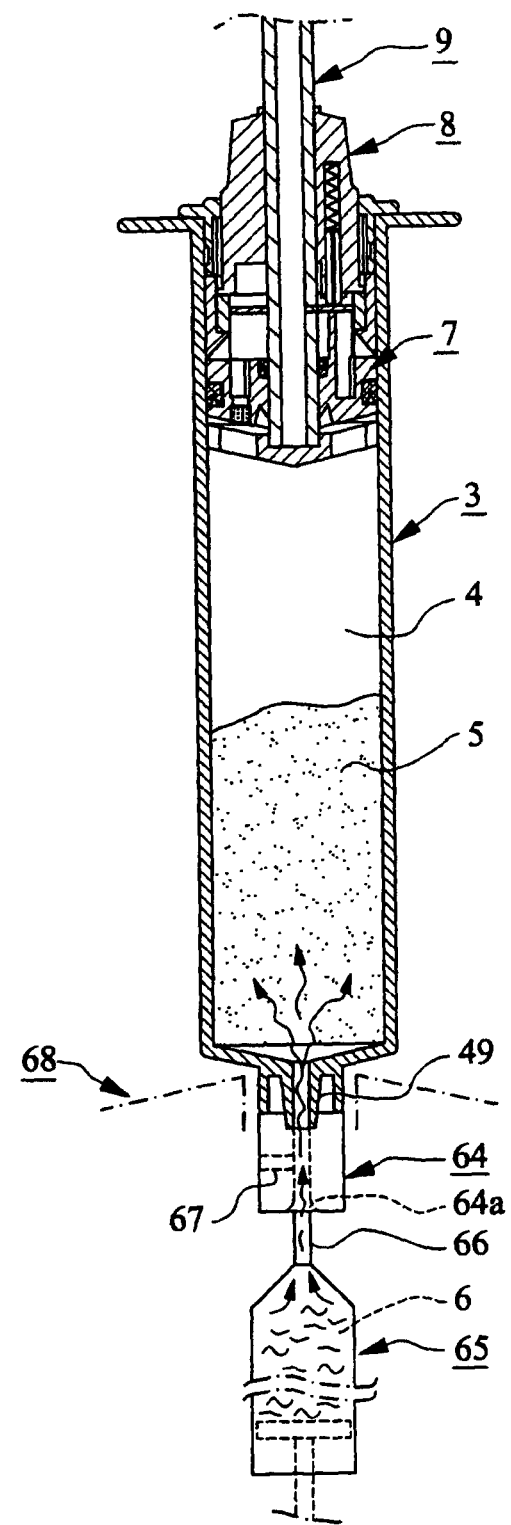
FIG. 9 illustrates a part of the device of FIG. 1 containing a powder component and during injection of a liquid component.

As is apparent from FIG. 9, the mixing space 4 of the mixing container 3 may carry the powder component 5 when the device 1 is delivered. The discharge opening 49 is hereby closed by a closing device 64 which prevents the powder component 5 from falling out of the mixing space 4.

The liquid component 6 can be provided in a liquid container 65 and can be fed into the mixing space 4 for mixing therein with the powder component 5.

The liquid container 65 has a discharge end 66 and the closing device 64 can be designed such that the discharge end 66 can open the closing device 64 when it is inserted into said device for injecting the liquid component 6 into the mixing space 4 and the powder component 5 therein. To this end, the closing device 64 may comprise a valve body 64a which is normally closed and which is opened by the discharge end 66 when said end is inserted into the closing device 64 and automatically returned to closed position when the discharge end 66 is removed or withdrawn from the closing device 64.

A valve 67 can be provided to cooperate with the closing device 64 to permit gas to escape from the mixing space 4 when the liquid component 6 is injected into said space from the liquid container 65. This valve 67 can be closed and may be opened when required.

In order to vibrate the content of the mixing space 4, i.e. the powder and liquid components 5, 6 and/or the mass 2, the mixing container 3 or parts thereof may be brought in contact with a vibrating device 68 schematically illustrated in FIG. 9.

Figure 10:
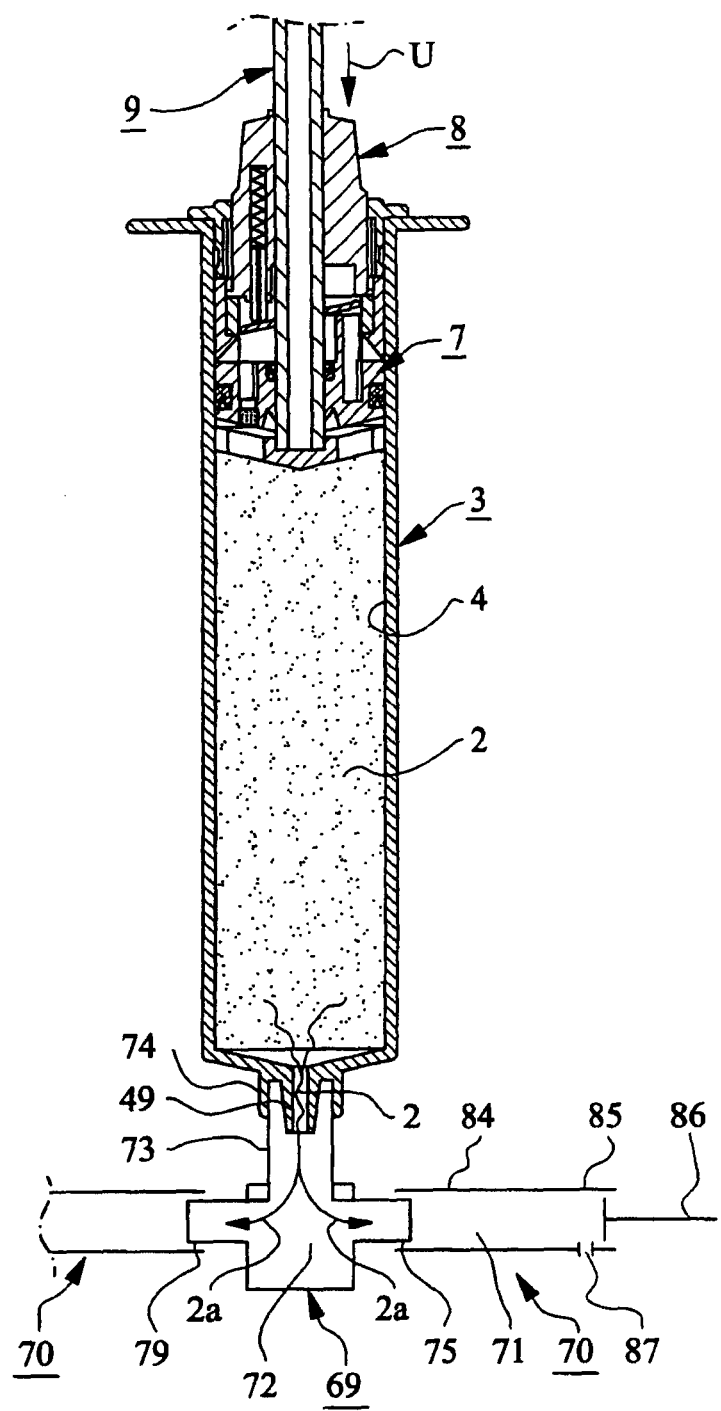
FIG. 10 illustrates a part of the device of FIG. 1 connected to a distributor device.
Figure 11:
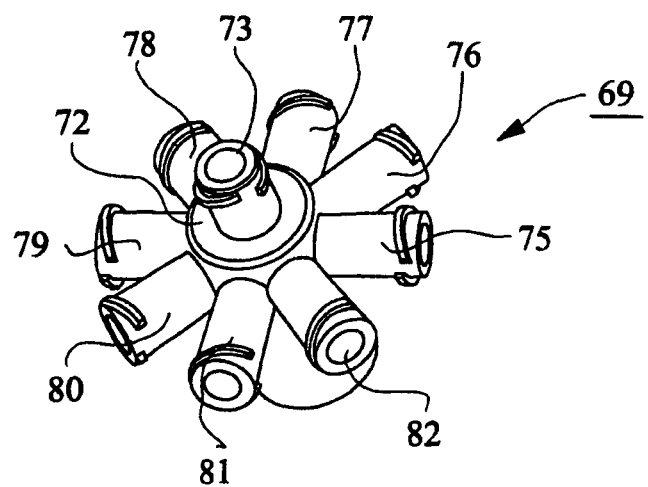
FIG. 11 is a perspective view of the distributor device of FIG. 10.
Figure 12:
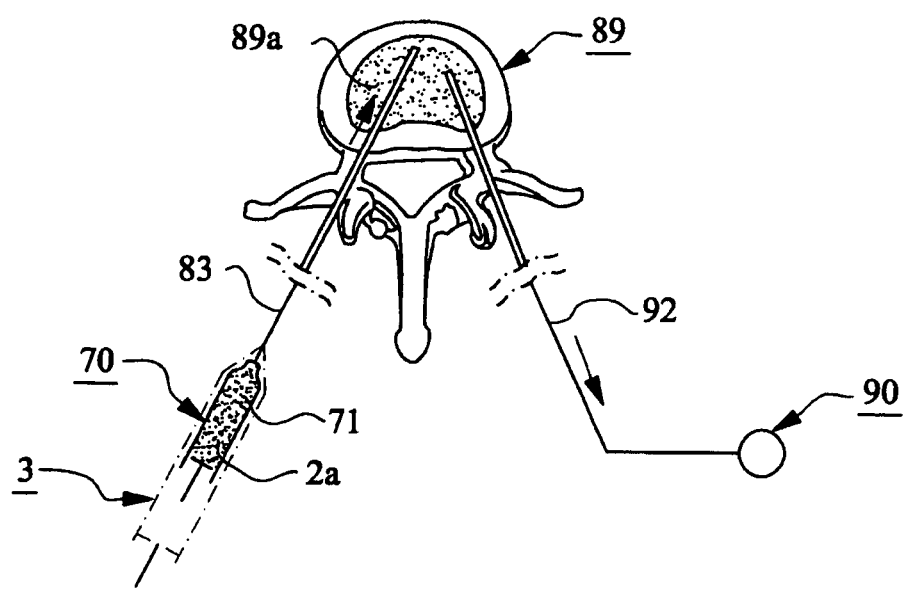
FIG. 12 illustrates the device of FIG. 1 during use in connection with vertebroplasty.

As is apparent from FIG. 10, the mixing container 3 can be connected to a distributor device 69 or vice versa. Several containers 70 can be connected thereto or vice versa, such that mass 2 mixed in the mixing space 4 can be fed out or discharged from said mixing space and into the distributor device 69. The distributor device 69 distributes the mass 2 to the various containers 70 such that portions of the mass 2 are fed into inner spaces 71 in the containers 70. The inner space 71 in each container 70 is substantially smaller than the mixing space 4 of the mixing container 3, which means that one can fill the spaces 71 of a plurality of containers 70, e.g. the spaces 71 of eight containers 70, with a part volume 2a of the mass 2 from the mixing space 4.

When the spaces 71 of the respective number of containers 70 are filled with said part volume 2a of the mass 2, each container 70 can be removed from the distributor device 69 or vice versa and the part volume 2a of mass 2 in the container 70 can be fed and/or sucked out of the container 70.

The distributor device 69 preferably comprises a distributor body 72 with an axial inlet pipe 73 which can be located close to such an outlet or discharge end 74 of the mixing container 3 having the discharge opening 49. The inlet pipe 73 can be located at the discharge end 74 by screwing on or in any other suitable manner such that inner passages in the distributor body 72 communicate with the discharge opening 49. Of course, the mixing container may instead be located on the inlet pipe 73.

The distributor device 69 may also comprise a number of discharge pipes 7582, at least two and e.g. eight pipes, which extend radially in a star-like manner from the distributor body 72 and which communicate with inner members of the distributor body 72.

Each container 70 has a front part 84 through which it can be mounted, e.g. screwed on to one of the discharge pipes 75-82 of the distributor device 69 or vice versa, such that a part volume 2a of mass 2 can be fed into the space 71. During this filling of the space 71, a piston 86 forming part of the container 70 is preferably located in a rear part 85 of the container 70. After the space 71 has been filled with the part volume 2a of mass 2, a cannula or needle 83 can be located on the front part 84. The part volume 2a of mass 2 is fed or sucked out of the space 71 of the container 70 through said cannula 83.

Each container 70 may eventually have an opening 87 which preferably is found in the rear part 85 and immediately in front of the piston 86 when said piston is situated in the rear part 85. This opening 87 allows gas in the space 71 of the container 70 to be pressed out of the space when said part volume 2a of mass 2 is fed into said space 71. Hereby, it is prevented that gas in the space 71 resists entrance of the part volume 2a of mass 2 into said space 71. The opening 87 has e.g. a diameter of 0.2-1.0 mm, preferably about 0.6 mm.

The opening 87 may alternatively be a groove (not shown) provided axially in the inner side of the container 70 and extending beyond the piston 86 when said piston is situated in the rear part 85 of the container 70.

When the required number of containers 70 have been filled with the part volume 2a of mass 2, one container 70 at the time is removed from the distributor device 69 and a cannula or needle 83 is mounted preferably on the front part 84 of the container 70 such that the part volume 2a of mass 2 can be fed or sucked out through the cannula 83 with or without support from the piston 86 until the space 71 is empty. By removing one container 70 at the time from the distributor device 69 and letting the other filled containers 70 remain mounted thereon, it is achieved that the mass 2 in the containers 70 not yet removed is not subjected to atmospheric air for an unnecessarily long time.

Since the size of the space 71 in each container 70 is known, one knows exactly how large a part volume 2a of mass 2 which is fed out of or discharged from each container 70. For treating spongy bone 89 with mass 2, said mass 2 can be sucked into inner parts 89a of the spongy bone 89. To this end, a container 70 is connected to the spongy bone 89 by inserting the cannula 83 thereof, or a member (not shown) to which the cannula 83 can be connected, into the inner parts 89a such that the space 71 of the container 70 communicates therewith. To said inner parts 89a of the spongy bone 89 there is also connected at least one vacuum source 90 through a connection line 92 for generating a vacuum in the inner parts 89a and in the space 71 of the container 70 connected thereto such that the part volume 2a of mass 2 is sucked out of said space 71 and through the cannula 83 into the inner parts 89a of the spongy bone 89. During this suction step, the piston 86 may eventually be displaced in the direction U for supporting the suction of the part volume 2a of the mass 2 out of the space 71.

Inner parts 89a of the spongy bone 89 can be provided with mass 2 from the mixing container 3. The mixing container 3 can be provided with a cannula or needle (not shown) or similar and this cannula is inserted into the inner parts 89a. The mass 2 can thereby be sucked out of the mixing space 4 of the mixing container 3 and into the inner parts 89a by means of the vacuum source 90. Eventually, this suction of mass 2 from the mixing space 4 may be supported by a displacement of the piston means 7 in the direction U.

The spongy bone 89 may e.g. be a spongy vertebra or an osteoporosis fracture in the form of a thighbone (femoral) or knee (patellar) fracture.

Mixed mass 2 in the mixing container 3 can be used for fixation of implants, whereby one can provide the container with a discharge pipe or similar (not shown), through which the mass 2 is discharged by means of the piston means 7 into cavities in the bone in which the implant shall be fixed.

The mass 2 may consist of bone substitute and/or bone reinforcing material which primarily consist of calcium base material or ceramics which can be mixed with a hardener, e.g. water. These substances may be selected from the group comprising calcium sulphate-α-hemihydrate, calcium sulphate-β-hemihydrate, calcium sulphate-dihydrate, calcium carbonate, α-tricalcium phosphate, hydroxyapatite, dicalcium phosphate-dihydrate, anhydrous dicalcium phosphate, tetracalcium phosphate, β-tricalcium phosphate, calcium deficient hydroxyapatite, monocalcium phosphate-monohydrate, monocalcium phosphate, calcium-pyurophosphate, precipitated hydroxyapatite, carbonaceous apatite (dahlite), octacalcium phosphate, amorphous calcium phosphate, oxyapatite, carbonato apatite and calcium aluminate.

A ceramic material may be calcium aluminate, which forms part of the product Doxa T from the company Doxa (www.doxa.se/pdf/nyhet_1.pdf).

X-ray contrast agents can be added to said ceramic bone substitute and/or bone reinforcing material, e.g. water soluble non-ionic X-ray contrast agents selected from the group comprising iohexol, ioversol, iopamidol, iotrolan, metrizamide, iodecimol, ioglucol, ioglucamide, ioglunide, iogulamide, iomeprol, iopentol, iopromide, iosarcol, iosimide, iotusal, ioxilan, iofrotal and iodecol.

Alternatively, the mass 2 can be a hardenable bone cement comprising polymer and monomer components. The polymer may be polymethylmethacrylate (PMMA) and the monomer methyl methacrylate (MMA). A polymer base material can be the product Cortoss™ from the company Orthovita in the U.S.A. For composition see www.orthovita.com/products/cortoss/oustechspecs.html. Another polymer base material can be the product SECOUR® Acrylic Resin PMMA from parallax medical Inc. (www.parallax-medical.com/go/91-92b550-5642_-1157-a432-d7a2b98310fe).

The mass 2 can be a bone substitute and/or bone reinforcing material and consist of a mineral and/or a ceramic in combination with polymer material.

The screw device 51 may be a device which can be connected to a mixing container 3 which is designed in another way than what is illustrated in the drawings and where the piston means 7 is located and operated in another way than what is shown in the drawings.

The distributor device 69 can be connected to a mixing container 3 or vice versa which is designed in another way than what is shown in the drawings and where the piston means 7 is mounted in another way than what is shown in the drawings.

The invention is not limited to the embodiments described above and illustrated in the drawings. As examples not described in detail, it should be mentioned that the mass 2 may be another type of mass than bone substitute and/or bone reinforcing material or bone cement or similar. The rotatable means 8 may cooperate with the piston means with other means than those shown and described; mixing may be carried through in another way than with a mixing means 9 and if there is such a means, this may be designed otherwise; the mixing container 3 may be designed in another way than what is described and illustrated; when using a screw device 51, this may be of another type than the one described and illustrated and this also refers to the distributor device 69. The piston means 7 may either be moved in the direction U by the mixing means 9 or be sucked in the same direction by the vacuum source 90, but it is also possible to move the piston means 7 by using the mixing means 9 and the vacuum source 90 simultaneously. The device 1 may be of the disposable type or used repeatedly.

The invention claimed is:

1. A screw device, the screw device comprising:
a first member that is non-rotatably connectable to a mixing container of an apparatus for producing a hardenable mass, the mixing container having a mixing space and a mixer to mix at least one powder and at least one liquid component to produce the hardenable mass;
a second member configured to be screwed into the first member so as to move a piston arranged in the mixing space, wherein the piston is provided to discharge the hardenable mass from the mixing space, wherein, when the second member is screwed into the first member, the screw device is configured to impart by screw device movements a discharge movement to the piston to discharge the hardenable mass from the mixing space;
wherein the second member is connectable to a part of the mixer of the mixing container, such that the second member linearly displaces the mixer when the second member is screwed into the first member;
wherein the second member is a pipe member with a multi-side nut;
wherein the pipe member has a longitudinal slit which is open in a lateral direction; and
wherein the multi-side nut has an open side such that the pipe member and the multi-side nut are configured to be threaded onto an elongated member of the mixer.

2. The screw device according to claim 1, wherein the first member is a nut-like member, and the second member is a screw-like member.

3. The screw device according to claim 1, wherein the part of the mixer is an operating handle of the mixer.

4. A mixing system for producing and discharging a hardenable mass, the system comprising:
a mixing container having a mixing space,
a mixer to mix at least one powder and at least one liquid component in the mixing space to produce the hardenable mass, wherein the mixer includes an elongated member;

a piston arranged in the mixing space for discharging the hardenable mass from the mixing space; and a screw device connectable to the mixing container such that the screw device is configured to impart by screw device movements a discharge movement to the piston for discharging the hardenable mass from the mixing space, wherein the screw comprises a first member that is non-rotatably connectable to the mixing container, wherein the screw device further includes a second member that is configured to be screwed into the first member so as to move the piston by screwing the second member into the first member, wherein the second member is a pipe member with a multi-side nut;

wherein the pipe member has a longitudinal slit that is open in a lateral direction; and wherein the multi-side nut has an open side such that the pipe member and the multi-side nut are configured to be threaded onto the elongated member of the mixer.

5. The mixing system of claim 4, wherein the first member is a nut-like member, and the second member is a screw-like member.

6. The mixing system according to claim 4, wherein the second member is adapted to engage at least a part of the mixer, such that the second member linearly displaces the mixer when the second member is screwed into the first member.

7. The mixing system according to claim 6, wherein the second member is connectable to the part of the mixer.

8. The mixing system according to claim 7, wherein the mixer includes an operating handle.

9. The mixing system according to claim 6, wherein the first member comprises a fork member that is connectable to a flange of the mixing container.

10. The mixing system according to claim 4, wherein the first member comprises a fork member that is connectable to a flange of the mixing container.

* * * * *